US00PP20073P2

(12) United States Plant Patent
Kanaya

(10) Patent No.: US PP20,073 P2
(45) Date of Patent: Jun. 9, 2009

(54) ***CALIBRACHOA* PLANT NAMED 'SUNBELRIAPU'**

(50) Latin Name: ***Calibrachoa* sp.**
Varietal Denomination: SUNBELRIAPU

(75) Inventor: Takeshi Kanaya, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/077,199

(22) Filed: Mar. 17, 2008

(51) Int. Cl.
*A01H 5/00* (2006.01)

(52) U.S. Cl. ..... Plt./413
(58) Field of Classification Search ..... Plt./413
See application file for complete search history.

*Primary Examiner*—S. B McCormick Ewoldt
(74) *Attorney, Agent, or Firm*—C. A. Whealy

(57) ABSTRACT

A new and distinct cultivar of *Calibrachoa* plant named 'Sunbelriapu', characterized by its outwardly spreading plant habit; vigorous growth habit; freely branching and flowering plant habit; long flowering period; and pink-colored flowers with red-colored centers and venation.

1 Drawing Sheet

Botanical designation: *Calibrachoa* sp.
Cultivar denomination: 'SUNBELRIAPU'.

BACKGROUND OF THE INVENTION

The present invention relates to a new and distinct cultivar of *Calibrachoa*, botanically known as *Calibrachoa* sp. and hereinafter referred to by the name 'Sunbelriapu'.

The new *Calibrachoa* is a product of a planned breeding program conducted by the Inventor in Higashiomi, Shiga, Japan. The objective of the breeding program is to develop new uniform *Calibrachoa* cultivars with attractive and unique flower coloration.

The new *Calibrachoa* originated from a cross-pollination conducted by the Inventor in Higashiomi, Shiga, Japan in April, 2003 of two unnamed proprietary selections of *Calbrachoa* sp., not patented. The cultivar Sunbelriapu was discovered and selected by the Inventor as a flowering plant from within the progeny of the stated cross-pollination in a controlled environment in Higashiomi, Shiga, Japan.

Asexual reproduction of the new *Calibrachoa* by vegetative cuttings in a controlled environment in Higashiomi, Shiga, Japan since September, 2005, has shown that the unique features of this new *Calibrachoa* are stable and reproduced true to type in successive generations.

SUMMARY OF THE INVENTION

The cultivar Sunbelriapu has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunbelriapu'. These characteristics in combination distinguish 'Sunbelriapu' as a new and distinct cultivar of *Calibrachoa*:

1. Outwardly spreading plant habit.
2. Vigorous growth habit.
3. Freely branching and flowering plant habit.
4. Long flowering period.
5. Pink-colored flowers with red-colored centers and venation.

Plants of the new *Calibrachoa* can be compared to plants of the female parent selection. Plants of the new *Calibrachoa* differ from plants of the female parent selection in the following characteristics:

1. Plants of the new *Calibrachoa* are not as trailing as plants of the female parent selection.
2. Plants of the new *Calibrachoa* have narrower leaves than plants of the female parent selection.

Plants of the new *Calibrachoa* can be compared to plants of the male parent selection. Plants of the new *Calibrachoa* differ from plants of the male parent selection in the following characteristics:

1. Plants of the new *Calibrachoa* have larger leaves than plants of the male parent selection.
2. Plants of the new *Calibrachoa* have larger flowers than plants of the male parent selection.

Plants of the new *Calibrachoa* can also be compared to plants of the cultivar Sunbel-Apu, disclosed in U.S. Plant Pat. No. 14,385. In side-by-side comparisons conducted in Higashiomi, Shiga, Japan, plants of the new *Calibrachoa* and the cultivar Sunbel-Apu differed in the following characteristics:

1. Plants of the new *Calibrachoa* were shorter and had shorter internodes than plants of the cultivar Sunbel-Apu.
2. Plants of the new *Calibrachoa* were more freely flowering than plants of the cultivar Sunbel-Apu.
3. Plants of the new *Calibrachoa* had larger flowers than plants of the cultivar Sunbel-Apu.
4. Plants of the new *Calibrachoa* and the cultivar Sunbel-Apu differed in flower color as plants of the cultivar Sunbel-Apu had yellowish pink-colored flowers.

BRIEF DESCRIPTION OF THE PHOTOGRAPHS

The accompanying colored photographs illustrate the overall appearance of the new *Calibrachoa*, showing the colors as true as it is reasonably possible to obtain in colored reproductions of this type. Colors in the photographs may differ slightly from the color values cited in the detailed botanical description which accurately describe the colors of the new *Calibrachoa*.

The photograph at the top of the sheet comprises a side perspective view of a typical flowering plant of 'Sunbelriapu' grown in a container.

The photograph at the bottom of the sheet comprises a close-up view of typical flowers of 'Sunbelriapu'.

DETAILED BOTANICAL DESCRIPTION

The aforementioned photographs and following observations, measurements and values describe plants grown in Higashiomi, Shiga, Japan, under commercial practice during the late spring and summer in a polyethylene-covered greenhouse. During the production of the plants, day temperatures averaged 23° C. and night temperatures averaged 13° C. Plants had been growing for about four months when the photographs and description were taken. In the following description, color references are made to The Royal Horticultural Society Colour Chart, 2001 Edition, except where general terms of ordinary dictionary significance are used.

Botanical classification: *Calibrachoa* sp. cultivar Sunbelriapu.

Parentage:

Female, or seed, parent. —Unnamed proprietary selection of *Calibrachoa* sp., not patented.

*Male, or pollen, parent.*—Unnamed proprietary selection of *Calibrachoa.* sp., not patented.

Propagation:

*Type.*—By vegetative cuttings.

*Time to initiate roots.*—About one week at 20° C. to 25° C.

*Time to produce a rooted young plant.*—About three weeks at 20° C. to 25° C.

*Root description.*—Fine, fibrous, fleshy; light brown in color.

*Rooting habit.*—Freely branching.

Plant description:

*Plant and growth habit.*—Outwardly spreading plant habit; mounding. Freely branching with lateral branches potentially forming at every node; pinching enhances lateral branch development. Vigorous growth habit.

*Plant height.*—About 12.3 cm.

*Pant diameter.*—About 34 cm.

Lateral branch description:

*Length.*—About 16.8 cm.

*Diameter.*—About 1.2 mm.

*Internode length.*—About 8 mm.

*Strength.*—Strong.

*Aspect.*—Upright to outward.

*Texture.*—Pubescent.

*Color.*—Close to 144A.

Foliage description:

*Arrangement.*—Alternate, simple.

*Length.*—About 2.2 cm.

*Width.*—About 6 mm.

*Shape.*—Narrowly elliptic.

*Apex.*—Broadly acute.

*Base.*—Obtuse.

*Margin.*—Entire.

*Texture, upper and lower surfaces.*—Pubescent.

*Venation pattern.*—Pinnate; reticulate.

*Color.*—Developing foliage, upper surface: Close to 138A. Developing foliage, lower surface: Close to 138B. Fully expanded foliage, upper surface: Close to 137A; venation, close to 144B. Fully expanded foliage, lower surface: Close to 137C; venation, close to 144B.

*Petiole.*—Length: About 6 mm. Diameter: About 1.7 mm. Texture, upper and lower surfaces: Sparsely pubescent. Color, upper and lower surfaces: Close to 144B.

Flower description:

*Flower arrangement and habit.*—Single salverform flowers arising from upper leaf axils. Freely flowering habit with usually about two open flowers per lateral branch. Flowers face upright or outwardly. Flowers not fragrant.

*Natural flowering, season.*—Plants of the new *Calibrachoa* initiate and develop flowers about three to four weeks after planting. Long flowering period; flowering commences naturally during the spring and plants flower continuously throughout the summer until late autumn in Japan.

*Flower longevity.*—Individual flowers last about seven to ten days on the plant. Flowers not persistent.

*Flower diameter.*—About 2.9 cm.

*Flower length* (*depth*).—About 2.9 cm.

*Throat diameter.*—About 7 mm.

*Tube length.*—About 1.5 cm.

*Tube diameter.*—About 1.5 mm.

*Flower bud.*—Shape: Cylindrical. Length: About 2 cm. Diameter: About 4.8 mm. Color: Close to 37C.

*Corolla.*—Arrangement: Five petals fused at the base and opening into a flared trumpet. Petal length from throat: About 1.1 cm. Petal width: About 1.3 cm. Petal shape: Spatulate. Petal apex: Rounded with truncate tendencies. Petal margin: Entire. Petal texture, upper and lower surfaces: Smooth, glabrous; velvety. Throat texture: Smooth, glabrous. Tube texture: Pubescent. Color: Petal, when opening, upper surface: Close to 49A; towards the throat, close to 46A; venation, close to 42B. Petal, when opening, lower surface: Close to 36A; venation, close to N34C. Petal, fully opened, upper surface: Close to 49C; towards the throat, close to 46B; venation, close to N34C; color becoming closer to 27A with development. Petal, fully opened, lower surface: Close to 69D; venation, close to 61B. Throat: Close to 12A. Tube: Close to 12C; venation, close to N200A.

*Calyx.*—Arrangement: One star-shaped calyx tube with five sepals fused at the base per flower. Sepal length: About 6.7 mm to 10 mm. Sepal width: About 2.8 mm. Sepal shape: Lanceolate. Sepal apex: Acute. Sepal margin: Entire. Sepal texture, upper and lower surfaces: Pubescent. Color, immature and mature, upper surface: Close to 137C. Color, immature and mature, lower surface: Close to 137C.

*Peduncles.*—Length: About 1.5 cm. Diameter: About 0.5 mm. Angle: Upright to outward. Strength: Strong. Texture: Smooth, glabrous. Color: Close to 144A.

*Reproductive organs.*—Stamens: Quantity/arrangement: Five per flower. Stamen length: About 8.2 mm to 11.9 mm. Anther shape: Ellipsoidal. Anther size: About 1.3 mm by 1.3 mm. Anther color: Close to 13C. Pollen amount: Moderate. Pollen color: Close to 12B. Pistils: Quantity: One per flower. Pistil length: About 1.1 cm. Style color: Close to 144D. Stigma shape: Transversely ellipsoidal. Stigma color: Close to 144B. Ovary color: Close to 144B.

*Seed/fruit.*—Seed and fruit development have not been observed on plants of the new *Calibrachoa*.

Temperature tolerance: Plants of the new *Calibrachoa* have been observed to tolerate temperatures from about 5° C. about 35° C.

Pathogen/pest resistance: Plants of the new *Calibrachoa* have not been observed to be resistant to pests and pathogens common to *Calibrachoa*.

It is claimed:

1. A new and distinct *Calibrachoa* plant named 'Sunbelriapu' as illustrated and described.

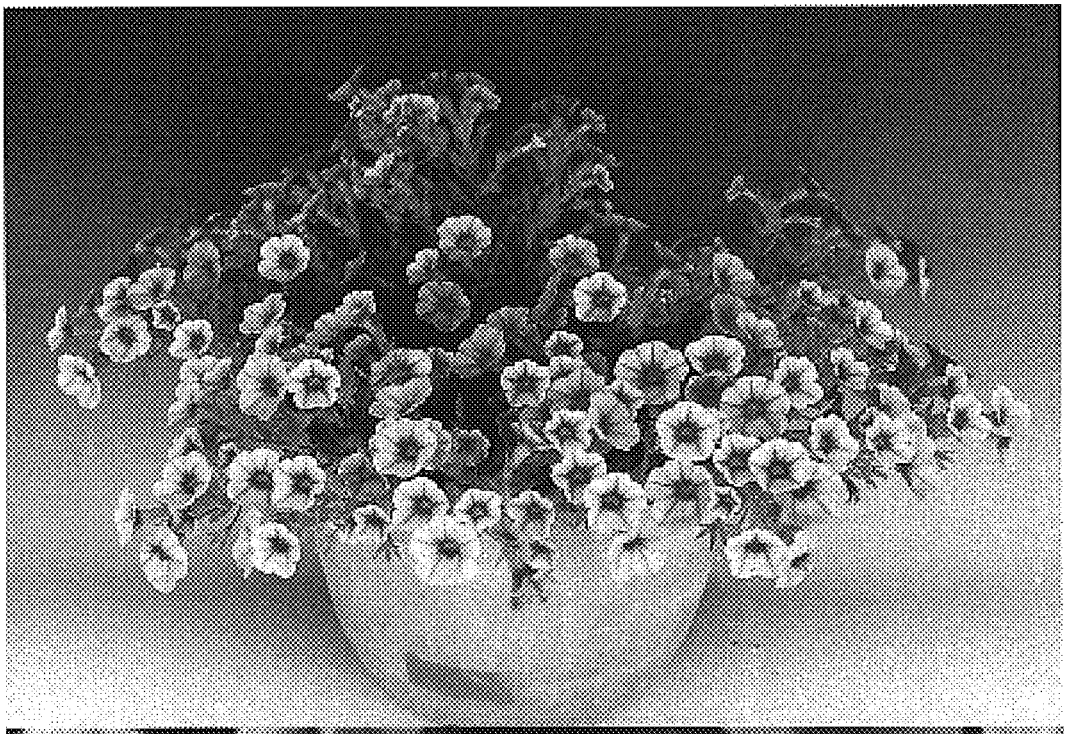
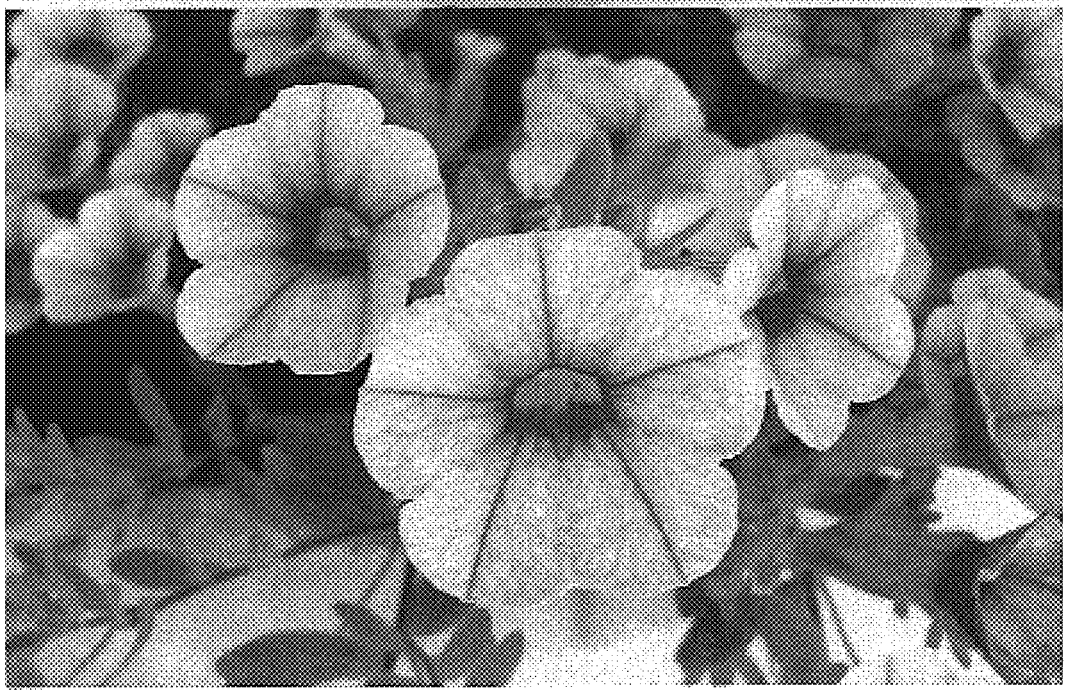

* * * * *